United States Patent
Kim et al.

(10) Patent No.: US 11,576,976 B2
(45) Date of Patent: *Feb. 14, 2023

(54) METHOD OF TREATING CANCER BY USING SIRNA NANOCOMPLEXES

(71) Applicant: D. R. NANO CO., LTD., Seoul (KR)

(72) Inventors: Sehoon Kim, Seoul (KR); Ick Chan Kwon, Seoul (KR); Eunjung Lee, Seoul (KR)

(73) Assignee: D. R. NANO CO., LTD., Seoul (KR)

( * ) Notice: Subject to any disclaimer, the term of this patent is extended or adjusted under 35 U.S.C. 154(b) by 27 days.

This patent is subject to a terminal disclaimer.

(21) Appl. No.: 16/198,727

(22) Filed: Nov. 21, 2018

(65) Prior Publication Data

US 2019/0076543 A1    Mar. 14, 2019

Related U.S. Application Data

(63) Continuation-in-part of application No. 15/001,808, filed on Jan. 20, 2016, now Pat. No. 10,172,879.

(30) Foreign Application Priority Data

Jan. 21, 2015   (KR) .................. 10-2015-0010225

(51) Int. Cl.

| | |
|---|---|
| *A61K 47/69* | (2017.01) |
| *A61P 35/00* | (2006.01) |
| *C12N 15/113* | (2010.01) |
| *A61K 47/55* | (2017.01) |
| *A61K 47/54* | (2017.01) |
| *A61K 31/14* | (2006.01) |

(52) U.S. Cl.
CPC .............. *A61K 47/55* (2017.08); *A61K 31/14* (2013.01); *A61K 47/541* (2017.08); *A61K 47/549* (2017.08); *A61K 47/6907* (2017.08); *A61P 35/00* (2018.01); *C12N 15/113* (2013.01); *C12N 15/1135* (2013.01); *C12N 2310/14* (2013.01); *C12N 2310/3517* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 10,172,879 | B2 * | 1/2019 | Kim | A61K 47/34 |
| 2009/0312402 | A1 * | 12/2009 | Contag | A61K 9/5138 |
| | | | | 514/44 R |
| 2010/0120891 | A1 * | 5/2010 | Camby | C12N 15/1138 |
| | | | | 514/44 A |
| 2013/0052127 | A1 * | 2/2013 | Sasaki | A61K 47/645 |
| | | | | 424/1.29 |

OTHER PUBLICATIONS

Lee et al. Journal of Controlled Release 210, 105-114, May 2015 (Year: 2015).*

* cited by examiner

*Primary Examiner* — Brian Whiteman
(74) *Attorney, Agent, or Firm* — STIP Law Group, LLC

(57) ABSTRACT

The present invention is related to a method for treating cancer by using siRNA nanocomplex consisting of a nucleic acid molecule, a monocationic drug and a biocompatible polymer surfactant. The present nanocomplex can deliver an active ingredient (for example, a nucleic acid molecule and monocationic drug) into a cell/tissue of interest in a stable manner, and may be effectively applied for treating or detecting diverse disorders (practically, cancers).

11 Claims, 9 Drawing Sheets
Specification includes a Sequence Listing.

[Fig. 1a]
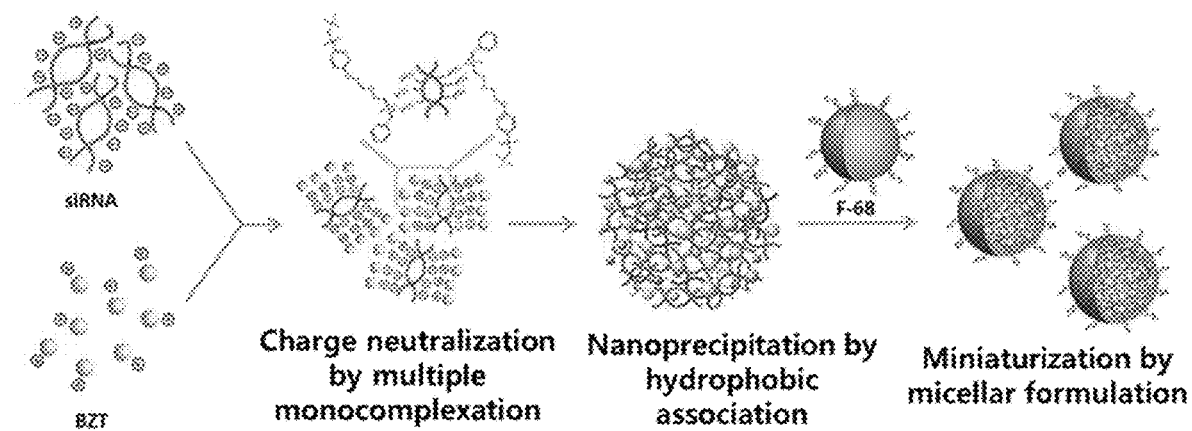
[Fig. 1b]
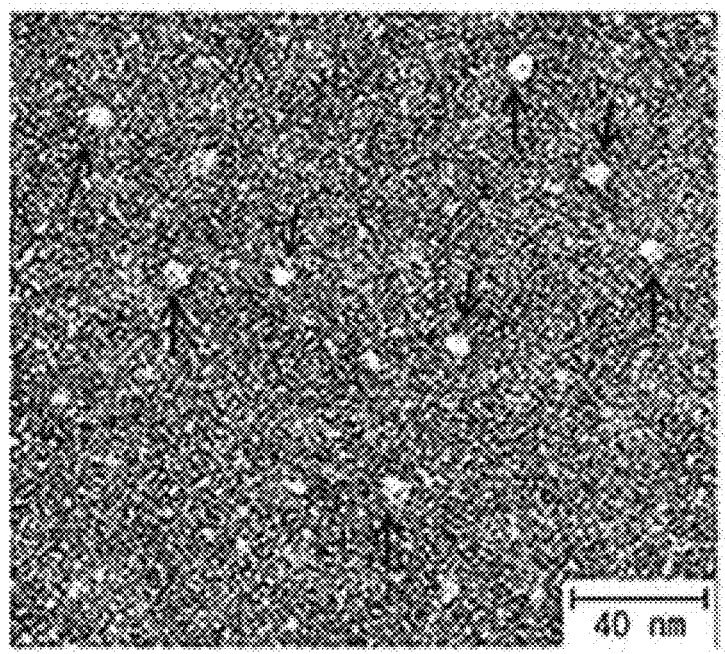

[Fig. 1c]
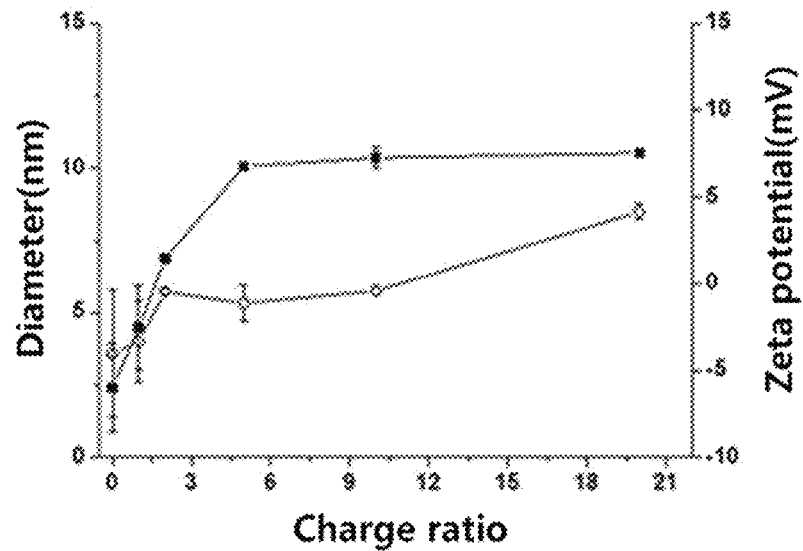
[Fig. 1d]
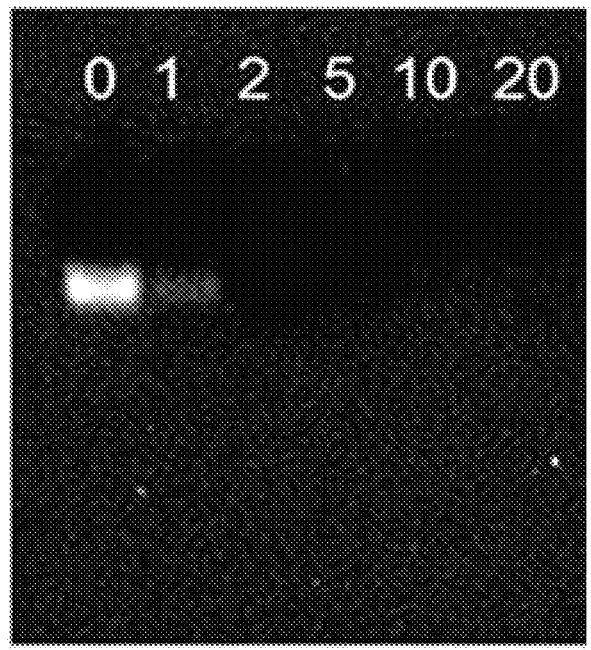

[Fig. 2]
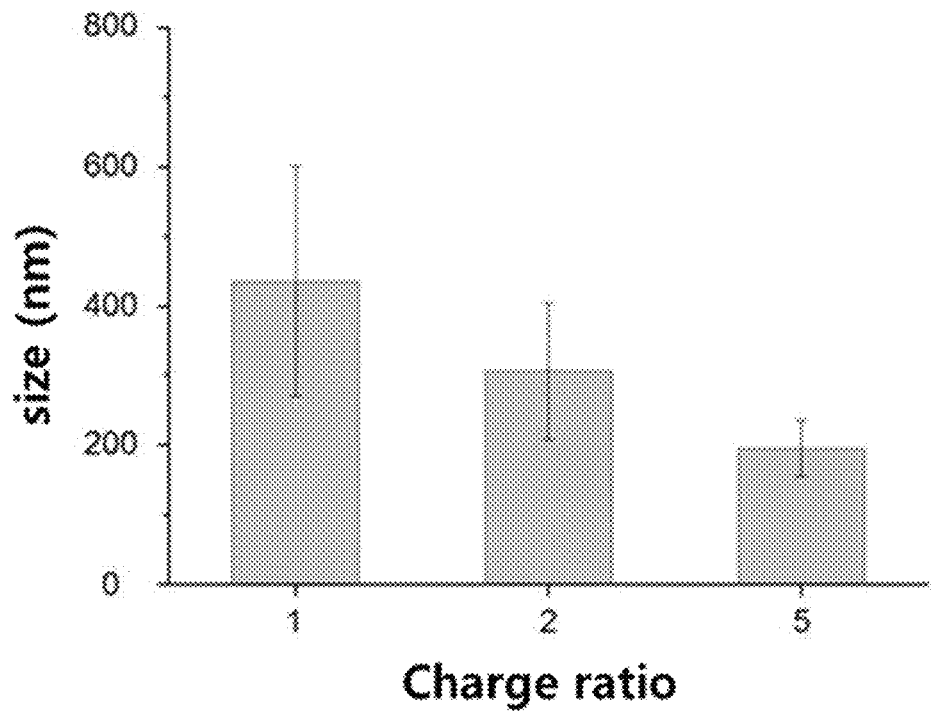
[Fig. 3a]
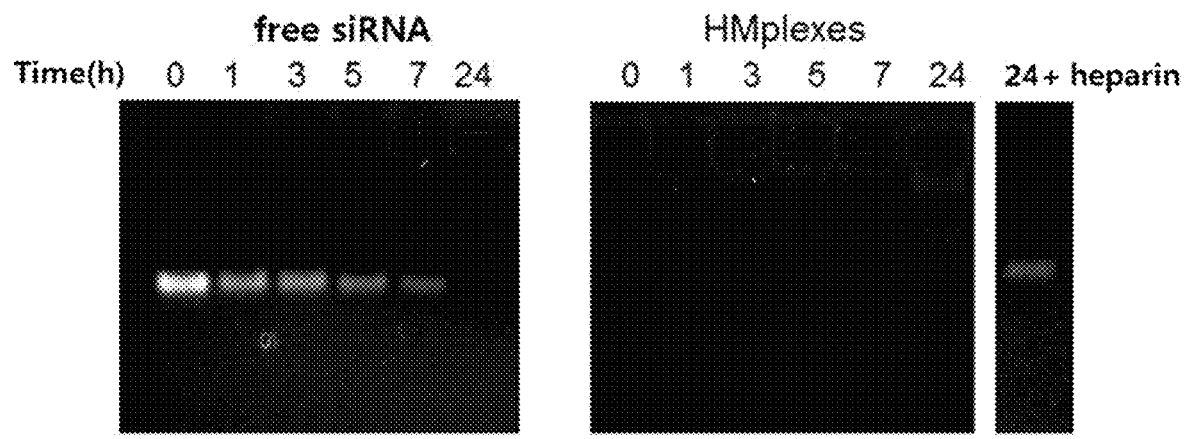

[Fig. 3b]
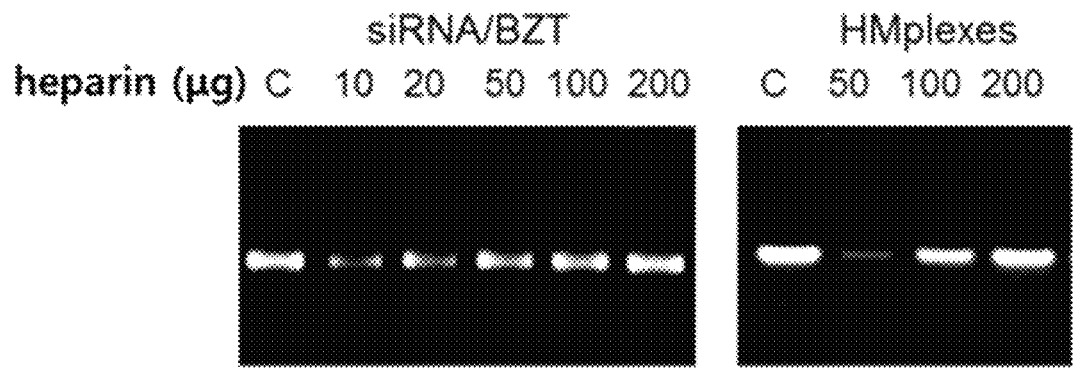
[Fig. 3c]
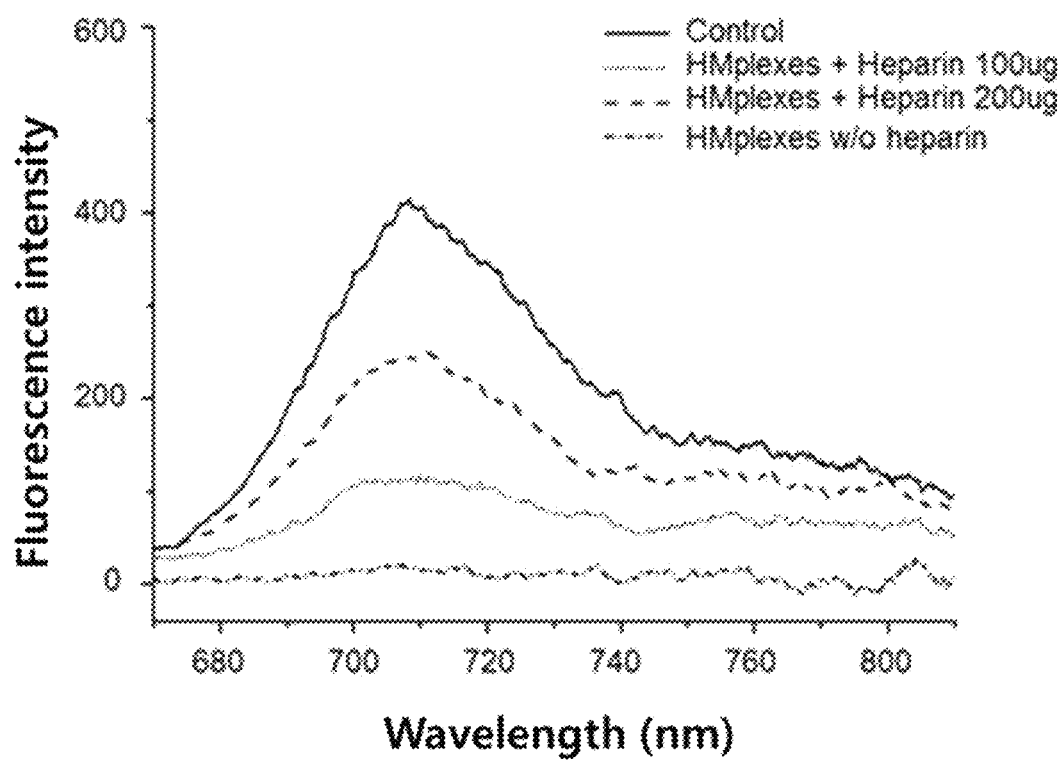

[Fig. 4]
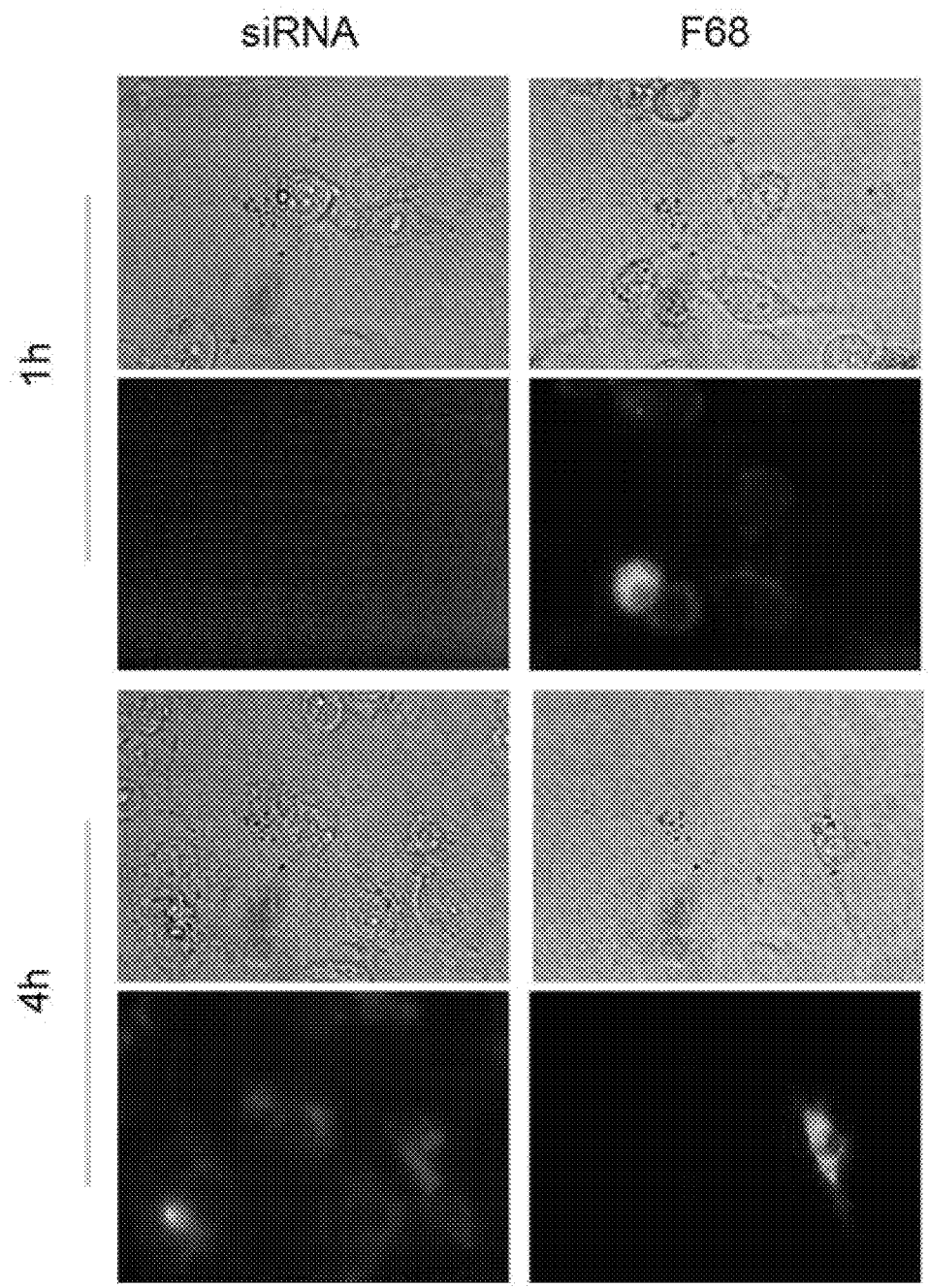

[Fig. 5]
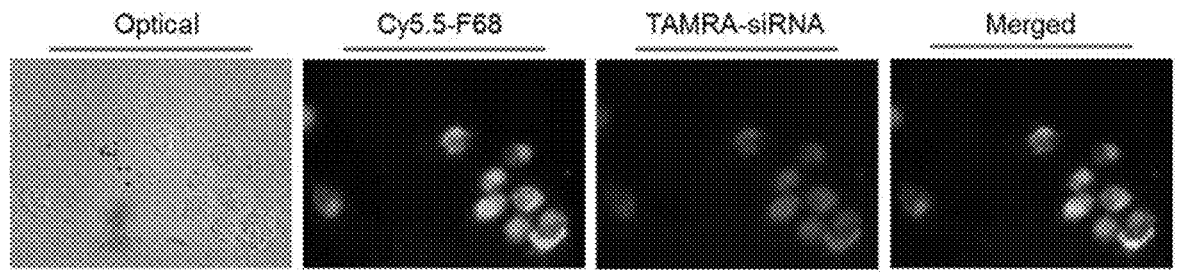
[Fig. 6a]
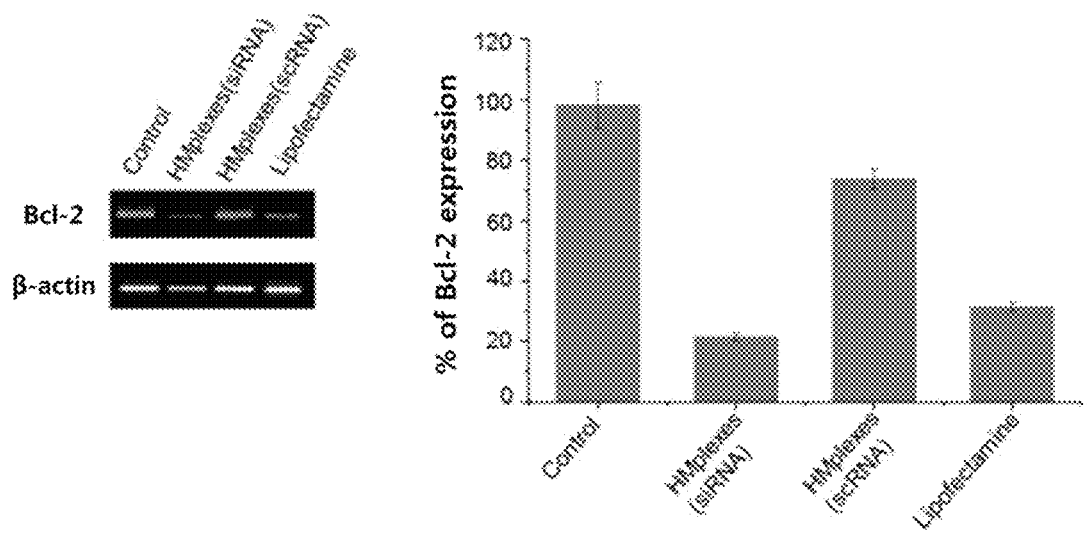
[Fig. 6b]
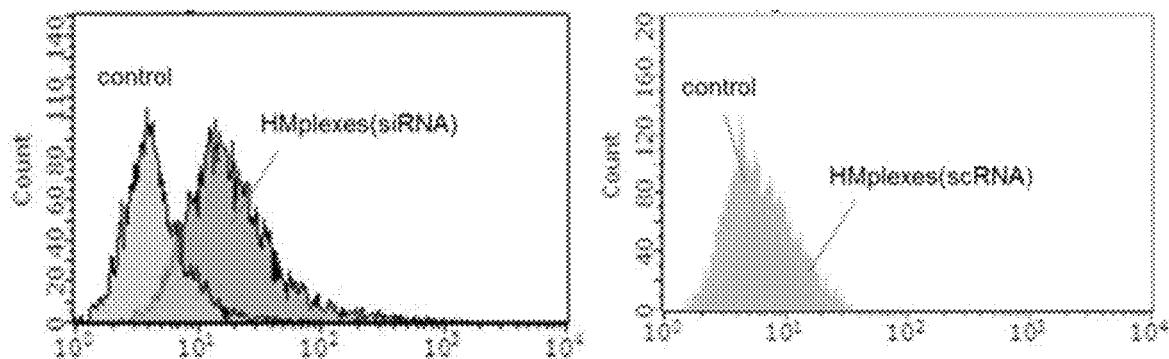

[Fig. 6c]
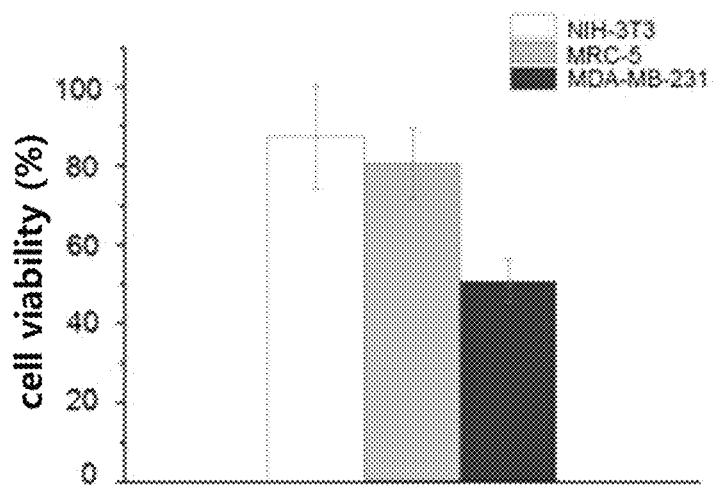
[Fig. 7a]
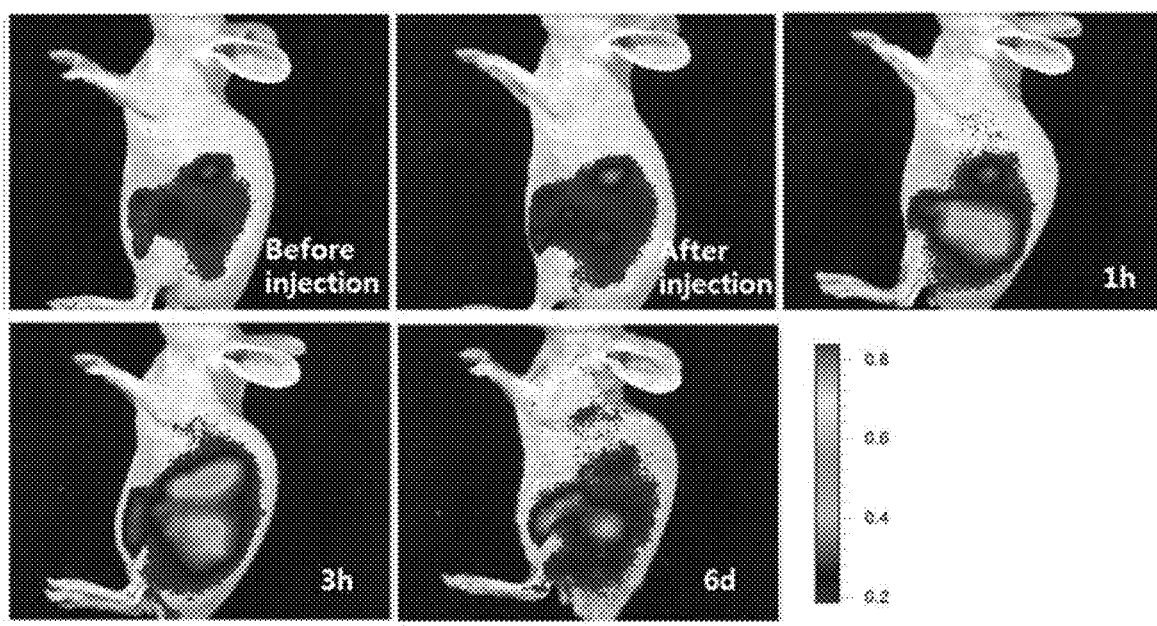

[Fig. 7b]
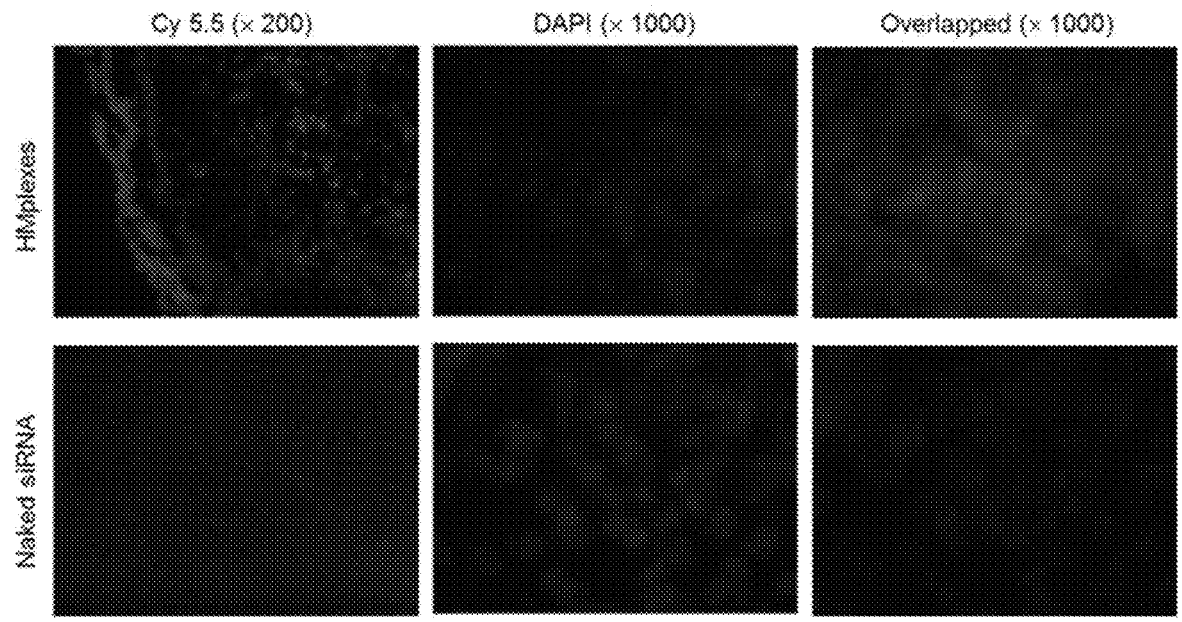
[Fig. 8]
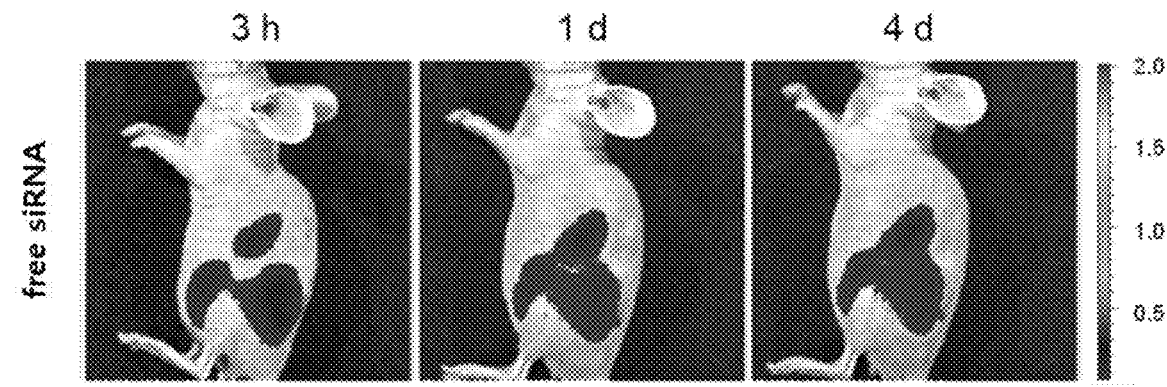

[Fig. 9a]
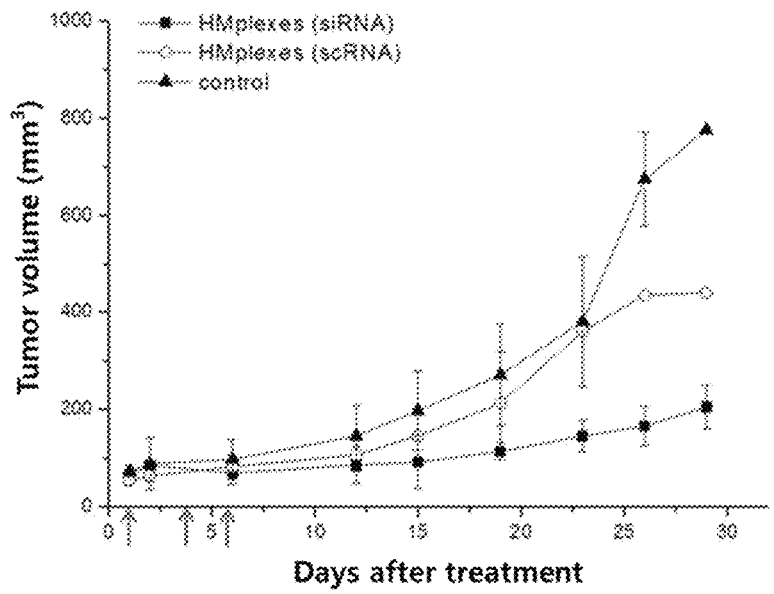
[Fig. 9b]
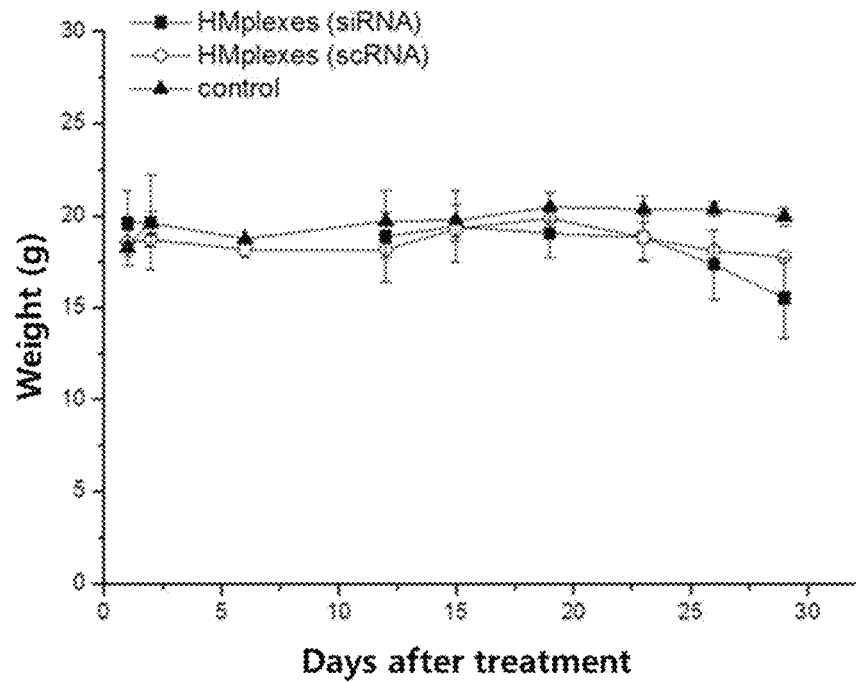

METHOD OF TREATING CANCER BY USING SIRNA NANOCOMPLEXES

CROSS-REFERENCE TO RELATED APPLICATION

This application is a Continuation-In-Part of application Ser. No. 15/001,808, filed Jan. 20, 2016, which in turn claims priority under 35 U.S.C. § 119 to Korean Application No. 10-2015-0010225, filed on Jan. 21, 2015, the contents of which is incorporated by reference herein in its entirety.

SEQUENCE LISTING

A SEQUENCE LISTING is submitted in a file named pus180073_ST25.txt via EFS Web and is hereby incorporated by reference in its entirety. Said file was created on Jan. 2, 2018 and is 1,403 bytes in size.

DESCRIPTION

Technical Field of this Invention

The present invention is related to a method for treating cancer by using siRNA nanocomplexes. The present nanocomplex consists of a nucleic acid molecule, a monocationic drug and a biocompatible polymer surfactant.

Background of this Invention

Since the discovery of RNA interference (RNAi), small interfering RNAs (siRNAs) have been exploited as a new potential therapeutic strategy. Among promising applications of siRNA is down-regulation of drug resistance pathways developed in aggressive cancer cells, which enables targeted therapy of specific tumor types with poor prognosis. Combining such gene-targeting siRNA with anticancer agents through a co-delivery system can disarm the resistant cells to greatly improve the treatment efficacy of chemotherapy (chemosensitization). From a clinical viewpoint, however, the development of siRNA therapeutics is limited by a lack of suitable nonviral delivery systems. Although many attempts have been made in similar ways applied to DNA delivery, they are not fully suited to the delivery of siRNA as it has different physicochemical features such as short chain length and rigid backbone structure compared to DNA. The typical mechanism for nanoscopic gene packaging has been primarily based on the electrostatic polycomplexation between polyanionic genes and complexing agents (cationic polymers or liposomes). In addition, previous studies revealed that the electrostatic interaction between DNA and monocationic surfactants can produce organic-soluble complexes to make water-insoluble functional solids. In these complexes, each anionic charge along the polyanionic DNA backbone undergoes monocomplexation with a cationic surfactant molecule. As a result, every single chain of DNA is surrounded with a number of surfactants by multiple monocomplexation and the overall charge neutralization induces solubility reversal to produce surfactant-jacketed hydrophobized DNA chains with organic solubility. However, the resulting polyplex/lipoplex systems in clinical applications have diverse problems, for example including need on a high molar ratio of cytotoxic cationic agent-to-siRNA necessary for complete complexation according to inefficient/loose packaging of short/rigid siRNA. Accordingly, there has been a demand on a siRNA/drug co-delivery system for clinical applications in an effective manner.

Throughout this application, several patents and publications are referenced and citations are provided in parentheses. The disclosure of these patents and publications in their entities are hereby incorporated by references into this application in order to more fully describe this invention and the state of the art to which this invention pertains.

SUMMARY OF THIS INVENTION

The present inventors have done intensive studies to develop a method for treating cancer disease by efficiently delivering a nucleic acid molecule of interest into a cell. As results, we have discovered that a ternary nanocomplex was formulated by encapsulating with a biocompatible polymer surfactant (for example, Pluronic F-68) the multiple monocomplex in which a nucleic acid molecule (for example, siRNA) and a monocationic drug (for example, benzethonium chloride as a kind of anticancer agent) were complexed each other, and the nanocomplex may be penetrated into a cell (practically, a tumor cell) in a feasible and stable manner, thereby exhibiting a remarkably synergistic effect on a cell/tissue of interest by the co-delivered therapeutics (i.e., the nucleic acid molecule and the monocationic drug), which results in very effective treatment for cancers.

Accordingly, it is an object of this invention to provide a method for treating cancers very effectively by delivering siRNA nanocomplexes into an interest cell.

It is another object of this invention to provide a pharmaceutical composition for treating a cancer.

It is another object to this invention to provide a drug delivery system for gene therapy.

It is still another object to this invention to provide a method for simultaneous delivery of a nucleic acid and a chemical drug into cancer cells or a tumor tissue.

Other objects and advantages of the present invention will become apparent from the following detailed description together with the appended claims and drawings.

In one aspect of this invention, there is provided a nanocomplex comprising: (a) a hydrophobically associated multiple monocomplex (HMplex) consisting of (i) a nucleic acid molecule having a targeting moiety; and (ii) a monocationic drug; and (b) a biocompatible polymer surfactant encapsulating the multiple monocomplex.

In another aspect of this invention, there is provided a pharmaceutical composition for treating a cancer comprising the aforementioned nanocomplex.

In still another aspect of this invention, there is provided a drug delivery system comprising the aforementioned nanocomplex.

The present inventors have done intensive studies to develop a method for efficiently delivering a nucleic acid molecule of interest into a cell. As results, we have discovered that a ternary nanocomplex was formulated by encapsulating with a biocompatible polymer surfactant (for example, Pluronic F-68) the multiple monocomplex in which a nucleic acid molecule (for example, siRNA) and a monocationic drug (for example, benzethonium chloride as a kind of anticancer agent) were complexed each other, and the nanocomplex may be penetrated into a cell (practically, a tumor cell) in a feasible and stable manner, thereby exhibiting a remarkably synergistic effect on a cell/tissue of interest by the co-delivered therapeutics (i.e., the nucleic acid molecule and the monocationic drug).

A disorder treatment using a gene has become a powerful tool after human genome project has been completed. That is to say, there have been made various attempts for treating a specific disorder by regulating the expression of a gene known to induce the specific disorder (for example, a method for treating a cancer by inhibiting the expression of Bcl-2 gene which was overexpressed in the cancer). This attempt may be functioned as a very effective and convenient therapy, but the prerequisite therefor is to deliver into a target cell/tissue an active ingredient for regulating (increasing or inhibiting) the expression of the gene.

To develop a clinically applicable drug delivery system, the present inventors have prepared the nanocomplex of this invention on the basis of the fact that a nucleic acid molecule could be protected from an external environment through a solubility reversal shown in the complex that is formed by an electrostatic interaction between the multianionic nucleic acid molecule and a cationic surfactant.

The nanocomplex of this invention consists of three components: (a) a nucleic acid molecule having a targeting moiety; (b) a monocationic drug; and (c) a biocompatible polymer surfactant.

Specifically, the present invention provides a method for simultaneously delivering a nucleic acid and a chemical drug into cancer cells or a tumor tissue, comprising the steps of: (a) administering a subject in need thereof the aforementioned nanocomplex; and (b) measuring fluorescence in the cancer cells or tumor tissue of the subject.

In addition, the present invention provides a method for simultaneously delivering a nucleic acid and a chemical drug into cancer cells or a tumor tissue, comprising the steps of: (a) administering a subject in need thereof the aforementioned nanocomplex; and (b) examining the delivery of siRNA nanocomplex by measuring fluorescence from a fluorescent pigment in the cancer cells or tumor tissue of the subject.

The term "targeting moiety" used herein means a nucleotide sequence that inhibits the expression of an oncogenic gene or a transcript thereof, wherein the nucleic acid molecule is a motif sequence of binding to the oncogenic gene to prevent the expression thereof. For example, when the present nanocomplex targets a cancer, the targeting moiety is bound to the transcript of an oncogenic gene (i.e., mRNA) to produce double-stranded mRNA, thereby enabling to inhibit the expression of the oncogenic gene. In other words, when utilizing the nanocomplex of this invention in a cancer therapy, the nucleic acid molecule of the present invention may target certain oncogenic gene. The oncogenic gene is known in the art to exert an influence in formation, maintenance, proliferation, death or survival of cancers, for instance including Bcl-2, Bcl-3, Bcl-4, Bcl-5, Bcl-6, HER2/Neu, HER3, HER4, raf, c-fos, c-jun, c-myc, c-kit, c-met, c-ret, Akt, hTERT, erbB, Sis, src, mdm2, abl, flt3, API, AMLI, axl, alk, fins, fps, gip, Ick, MLM, PRAD-I and trk, but is not limited to.

The nucleic acid molecule containing the targeting moiety of the present invention may be anyone with a multianionic property. In a certain embodiment, the nucleic acid molecule in the present nanocomplex includes siRNA, shRNA, miRNA, an antisense oligonucleotide, an aptamer, a ribozyme and a DNAzyme, and more practically, siRNA.

In a certain embodiment, the gene targeted to the nanocomplex of the present invention is an oncogenic gene, and more practically, Bcl-2.

In a certain embodiment, the length of the nucleic acid molecule is in a nucleotide number of 100 or less, more practically 70 or less, much more practically 50 or less, still much more practically 40 or less, and most practically 20 to 30.

The term "siRNA" used herein refers to a short RNA duplex that enables to induce RNAi (RNA interference) via a cleavage of a particular mRNA. The siRNA of the present invention consists of a sense RNA strand having a sequence corresponding to mRNA of a target gene and an antisense RNA strand having a sequence complementary to mRNA of the target gene. siRNA may be utilized for an effective gene knock-down tool or a gene therapy because it can inhibit the expression of the target gene. In addition, the siRNA of this invention is not restricted to a RNA duplex of which two strands are completely paired, and may comprise non-paired portion such as mismatched portion with non-complementary nucleotides and bulge with no opposite nucleotides. The overall length of the siRNA is 10-100 nucleotides, practically 15-80 nucleotides, and most practically, 20-70 nucleotides. siRNA may comprise either blunt or cohesive end so long as it enables to silent the target gene expression due to its RNAi effect. The cohesive end may be prepared in 3'-end or 5'-end overhanging structure. The number of the protruding nucleotide is not limited. For example, the nucleotide number may be in a range of 1 to 8, and more practically 2 to 6. In addition, siRNA may include a low molecular RNA (for example, a natural-occurring RNA molecule such as tRNA, rRNA, viral RNA, or an artificial RNA molecule) in a protruding region of any end within an extent that the effect for preventing the expression of target gene may be preserved. Further, the terminal structure of siRNA is not necessary to have a cleavable structure at both ends, and any terminal portion of RNA duplex may be a stem-loop structure conjugated by a linker RNA. The length of linker is not specifically limited where the length is capable of forming a stem pair without difficulty.

The term "shRNA (small hairpin RNA or short hairpin RNA)" used herein means an RNA sequence that forms a rigid hairpin turn and consists of 50-70 nucleotides, which forms a stem-loop structure in vivo. The double stranded stem-loop is formed by constituting nucleotide pairs through complementary interaction of 19-29 nucleotides in a long RNA towards both loop portions of 5-10 nucleotides. The hairpin structure of shRNA is degraded to siRNA as cellular machinery, and then binds to a RNA-induced silencing complex. The aforementioned complex binds to mRNA matched to siRNA linked thereto, resulting in degradation of mRNA. shRNA is transcribed by RNA polymerase III, and the production of shRNA in mammalian cells may cause interferon responses like the way that cells recognize shRNA as a viral attack to find a protective tool.

The term "microRNA (miRNA)" used herein is a single-stranded RNA molecule of 21-25 nucleotides, which is bound to 3'-UTR of mRNA (messenger RNA) to control an eukaryotic gene expression and a single-stranded RNA molecule consists of full-length nucleotides of 21-23. In the production of miRNA, a pre-miRNA with a stem-loop structure is prepared by Drosha (RNaseIII type enzyme), and then translocated into cytoplasm to be cleaved by Dicer, resulting in producing mature miRNA. As described above, the prepared miRNA regulates the expression of a target protein to participate in development, cell proliferation and death, lipid metabolism, oncogenesis, and so forth.

The term "ribozyme" used herein is RNA with an activity such as an enzyme capable of cleaving a specific RNA in itself by recognizing a base sequence thereof as a kind of RNA. Ribozyme is a nucleotide sequence complementary to mRNA strand of interest and consists of: (a) a binding portion with specificity; and (b) a portion to cleave a target RNA. The term "aptamer" used herein refers to an oligonucleotide (generally, RNA molecule) bound to a specific target. Practically, "aptamer" in this specification means an oligonucleotide aptamer (for example, RNA aptamer).

The term "antisense oligonucleotide" used herein is intended to refer to DNA, RNA or its derivatives including nucleotide sequences complementary to those of a target mRNA, characterized in that they bind to a complementary sequence of the target mRNA and interfere its translation to protein. The antisense oligonucleotide of the present invention refers to DNA or RNA sequences which are complementary to mRNA of a target gene and bind to mRNA thereof, characterized in that they may bind to mRNA of the target gene and interfere their translation to protein, translocation into cytoplasm, maturation or essential activities to other biological functions. The length of antisense oligonucleotides is in a range of 6-100 nucleotides, practically 8-60 nucleotides, and more practically 10-40 nucleotides. In addition, the antisense oligonucleotides may be modified at above one or more positions of base, sugar or backbone.

The term "complementary" used herein refers to a sequence having sufficient complementarity to the extent that the targeting moiety of the nucleic acid molecule hybridizes or anneals selectively with the nucleotide sequence of the target (for example, Bcl-2 gene) under certain hybridization or annealing conditions, specifically physiological conditions (within a cell). The complementary sequence may include one or more mismatch nucleotide sequence. Further, the term "complementary" may encompass all of 'substantially complementary' and 'perfectly complementary', and more practically, 'perfectly complementary'.

Next, the nanocomplex of this invention includes a monocationic drug linked to the multianionic moiety of the present nucleic acid molecule. The drug capable of being utilizing for the nanocomplex of this invention may be applied as any material which has monocationic property and enables to form a stable monocomplex through an electrostatic interaction with the nucleic acid molecule. Conventionally, the nucleic acid molecule and a monocationic drug (or surfactant) are conjugated together to form monocomplex (for example, HMplex), and also contribute to formation of non-aqueous duplex complexes with a large hydrodynamic size (for example, 200-500 nm) by their self-assembly. Such sized complexes have problems such as a difficulty of cellular delivery (i.e., penetration) of an active ingredient in practical applications.

To overcome this, the present inventors have prepared a uniform colloidal formulation with a smaller size by encapsulating the duplex complexes using a biocompatible polymer surfactant (practically, micellar encapsulation) (See: FIG. 1), suggesting that three components consisting of nucleic acid molecule, monocationic drug and biocompatible polymer surfactant form a nanostructure by an electrostatic/hydrophobic interaction. Further, the nanocomplex has a micellar structure, thereby being capable of easily penetrating into a cell.

In a certain embodiment, the monocomplex is formed through a self-assembly of the nucleic acid molecule and the monocationic drug.

In a certain embodiment, a charge ratio of the nucleic acid molecule and the monocationic drug is in a range of 1:2 or more, more practically 1:3 or more, and much more practically 1:4 or more.

Still another technical feature of the present nanocomplex is that the monocationic drug not only has a structural function of aggregate formation, but acts as an active material. In conventional drug delivery systems, for example liposome-mediated drug delivery system, cationic lipid or polymer primarily functions as a vehicle for delivery of an active ingredient in the liposome. In contrast, in an illustrative Example of the present invention (for example, a case using an anticancer agent), the monocationic drug is aggregated with the nucleic acid molecule to form a rigid monocomplex which not only has an ability that protects the nucleic acid molecule from serum nucleases when administered into a physiological environment, i.e., into a body fluid, but also represents an anticancer activity in itself after the monocomplex is degraded according to delivery into a cell. Consequently, the nucleic acid molecule and the monocationic drug show a synergistic effect (See: FIGS. 6 and 9).

In a certain embodiment, the monocationic drug of the present invention is benzethonium chloride (BZT).

As further another important aspect, generally the biocompatible polymer surfactant used in the preparation of colloidal formulation may encapsulate HMplexes of the present invention with a large hydrodynamic size as a clinically applicable colloidal formulation. The biocompatible polymer surfactant used in the present nanocomplex may be utilized as any type of nanocomplex enabling to encapsulate the monocomplex of this invention (specifically, micellar encapsulation), and more practically, the biocompatible polymer surfactant includes polyoxyethylene-polyoxypropylene block copolymer, polyvinyl alcohol and gelatin, and much more practically, polyoxyethylene-polyoxypropylene block copolymer.

In a certain embodiment, the biocompatible polymer surfactant utilized in the present invention is non-ionic polyoxyethylene-polyoxypropylene block copolymer (poloxamer) represented by the following Chemical formula 1:

    Chemical formula 1

In the chemical formula, PE is ethylene oxide, PPO is propylene oxide, x, y and z represent independently an integer of 1-10,000, respectively.

The poloxamer has a tri-block structure composed of a hydrophobic center of polypropylene oxide and a hydrophilic poly tag at both ends of polyethylene oxide, and may be utilized for increasing water solubility of a hydrophobic oil material or enhancing a miscibility of two materials having different characteristics each other. According to the constitution of x, y and z, the poloxamer can be purchased from diverse pluronics trade marks (BASF Corporation), for example including pluronic F-38, F-68, F-77, F-98, F-108 and F-127, without limitation. Since poloxamer has an amphipathic structure, it is utilized for increasing water solubility of a hydrophobic oil material or enhancing a miscibility of two materials having different characteristics each other. Poloxamer has been applied in industrial, cosmetic or medical fields, and particularly has been made good use as a model system of drug delivery system. In addition, the addition of poloxamer allows cells to be under low stress conditions due to its cell cushioning effects, thereby enabling to be significantly utilized as a cell culture medium.

In a certain embodiment, the biocompatible polymer surfactant is pluronic F-68.

In a certain embodiment, the nanocomplex has a cell penetrating ability (See: FIG. 7a).

Additionally, the nucleic acid molecule or biocompatible polymer surfactant of the present invention may be labeled with a fluorescent moiety.

In a certain embodiment, the nanocomplex of the present invention has a hydrodynamic size of 50 nm or less, more practically 40 nm or less, much more practically 20 nm or less, and most practically 10 nm or less, and uniformly distributes as a colloidal form in an aqueous environment.

As described above, the nanocomplex of this invention may be variously applicable depending on a target (for example, a gene associated with a specific disorder) of the nucleic acid molecule and the monocationic drug. When applying to cancer therapy the pharmaceutical composition containing the present nanocomplex, the nucleic acid molecule and monocationic drug in the complex provide an anticancer function. In a certain embodiment, the nucleic acid molecule is to inhibit the expression of Bcl-2 as a target to be an oncogenic gene, and the monocationic drug is an anticancer agent, more practically benzethonium chloride (BZT).

In a certain embodiment, the cancer of this invention includes, but is not limited to, brain cancer, neuroendocrine cancer, stomach cancer, lung cancer, breast cancer, ovarian cancer, liver cancer, bronchial cancer, nasopharyngeal cancer, laryngeal cancer, pancreatic cancer, bladder cancer, adrenal cancer, colon cancer, colorectal cancer, cervical cancer, prostate cancer, bone cancer, skin cancer, thyroid cancer, parathyroid cancer and ureter cancer.

The pharmaceutical composition of the present invention includes a pharmaceutically acceptable carrier. The pharmaceutically acceptable carrier contained in the pharmaceutical composition of the present invention, which is commonly used in pharmaceutical formulations, but is not limited to, includes lactose, dextrose, sucrose, sorbitol, mannitol, starch, acacia rubber, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered parenterally (for example, peritumoral, intravenous, peritoneal, subcutaneous or local administration route).

In still another aspect of this invention, there is provided a method for simultaneous delivery of a nucleic acid and a chemical drug into cancer cells or a tumor tissue, comprising administering a subject in need thereof the aforementioned nanocomplex.

Since the present drug delivery method comprises the nanocomplex of this invention as active ingredients described above, the common descriptions between them are omitted in order to avoid undue redundancy leading to the complexity of this specification.

Specifically, the present invention may provide a method for simultaneously delivering a nucleic acid and a chemical drug into cancer cells or a tumor tissue, comprising the steps of: (a) administering a subject in need thereof the aforementioned nanocomplex; and (b) measuring fluorescence from a fluorescent pigment in the cancer cells or tumor tissue of the subject.

In a certain embodiment, the nanocomplex of the present invention is administered into a tumor tissue parenterally, and more practically by peritumoral, intravenous or peritoneal administration route.

In a certain embodiment, the subject capable of applying the present method includes a mammal, more practically human, mouse, rat, guinea pig, rabbit, monkey, pig, horse, cattle, sheep, antelope, dog and cat, but is not limited to.

After the nanocomplex of the present invention is administered into a subject, the nanocomplex-derived fluorescence is detected in a cell/tissue of interest. Specifically, the nucleic acid molecule or biocompatible polymer surfactant in the present nanocomplex may be labeled with a fluorescent moiety, and the target may be detected in a convenient and feasible manner using the fluorescence therefrom.

In a certain embodiment, the nucleic acid molecule or biocompatible polymer surfactant of the present invention may be selectively linked or conjugated with a fluorescent moiety such as a fluorescent pigment or a derivative thereof that have as a basic backbone at a terminal end rhodamine, cumarin, cyanin, EvoBlue, oxazine, carbopyronin, naphthalene, biphenyl, anthracene, phenantrene, pyrene, carbazole, and so on. For example, the fluorescent moiety of this invention may be linked with Cy5.5 (694), ATTO 390™ (479). ATTO 425™ (484), ATTO 465™ (508), ATTO 488™ (523), ATTO 495™ (527), ATTO 520™ (538), ATTO 532™ (553), ATTO Rho6G™ (570), ATTO 550™ (576), ATTO 565™ (592), ATTO Rho3B™ (565), ATTO Rho11™ (608), ATTO Rho12™ (532), ATTO Thio12™ (579), ATTO 610™ (634), ATTO 611 X™ (681), ATTO 620™ (643), ATTO Rho14™ (625), ATTO 633™ (657), ATTO 647™ (669), ATTO 647 N™ (669), ATTO 655™ (684), ATTO Oxa12™ (663), ATTO 700™ (719), ATTO 725™ (752), ATTO 740™ (764), BODIPY TMR (568), BODIPY558/568 (568), BODIPY564/570 (570), EvoBlue10™, EvoBlue30™, MR121, Cy2™ (506), YO-PRO™-1 (509), YOYO™-1 (509), Calcein (517), FITC (518), FluorX™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), Cy3™ (570), Alexa™ 546 (570), TRITC (572), Magnesium Orange™ (575), phycoerythrin R&B (575), Rhodamine Phalloidin (575), Calcium Orange™ (576), pyronine Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanine (642), C-phycocyanine (648), TO-PRO™-3 (660), TOTO3 (660), DiD DiIC(5) (665), Cy5™ (670), thiadicarbocyanine (671), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705), Quasar 705 (610) and derivatives or conjugates thereof, without limitation. The number in parentheses indicates a maximum emission wavelength showing a nanometer unit. In addition, the fluorescent moiety derivative may further include free carboxyl group, ester (for example, N-hydrosuccinimde (NHS) ester) or maleimide derivatives unless interfering the formation of the present nanocomplex.

The term "fluorescent moiety" used herein means a fluorescent molecular, or a derivative or conjugate thereof creating a fluorescent signal by linked to or conjugated with the present nucleic acid molecule or biocompatible polymer surfactant. The term "link" or "chemical linkage (conjugation)" used herein refers to connect two components via at least one chemical bonding, and the chemical bonding may include, but is not limited to, any one known in the art, such as a covalent bond, a hydrogen bond, an ionic bond, a coordinate bond, and so forth, and practically a covalent bond.

To verify an effective delivery of a nucleic acid molecule or monocationic drug, the measurement of a target gene expression may be carried out, in addition to the fluorescence detection. The expression detection may be performed according to diverse methods well-known in the art. In a certain embodiment, the target gene expression targeted by the nucleic acid molecule in the present nanocomplex may be detectable by PCR (polymerase chain reaction). In a certain embodiment, the primers of this invention are utilized in gene amplification reactions.

PCR has been widely known as a nucleic acid amplification method, and various modifications and applications thereof have been developed. The term "amplification reaction" used herein refers to a reaction amplifying a nucleic acid molecule. Various amplification reactions have been reported in the art, including, but is not limited to, polymerase chain reaction (PCR), reverse transcription-polymerase chain reaction (RT-PCR), multiplex PCR, ligase chain reaction (LCR), Gap-LCR, repair chain reaction, transcription-mediated amplification, self-sustained sequence replication, selective amplification of target polynucleotide sequences, consensus sequence primed polymerase chain reaction (CP-PCR), arbitrarily primed polymerase chain reaction (AP-PCR), nucleic acid sequence based amplification (NASBA) and strand displacement amplification, which are incorporated herein by reference. Different amplification methods useful in the present method are described in various patent literatures.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. Specifically, the primer is a single-stranded deoxyribonucleotide. The primer used in the present invention may be comprised of a naturally occurring dNMP dAMP, dGMP, dCMP and dTMP), a modified nucleotide or a non-natural nucleotide. The primer may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

When performing the present method using primers, the gene amplification reactions are carried out and then mRNA from an object of interest (for example, a cancer cell or tumor tissue) is extracted and detected. Therefore, this invention basically utilizes mRNA in a sample as a template and performs a gene amplification reaction using primers capable of binding to mRNA or cDNA.

To obtain mRNA, total RNA is extracted from a sample (practically, cells). To collect total RNA may be carried out according to conventional methods published in several previous arts. For instance, total RNA in cells may be feasibly extracted using Trizol. Then, cDNA is synthesized from the extracted mRNA, followed by amplifying such cDNA. Since total RNA of this invention is separated from eukaryotic cells, the total RNA has poly-A tail at a terminus thereof. Thus, cDNA may be easily synthesized by oligo dT primers and reverse transcriptase using the sequence property. Afterwards, the synthesized cDNA is amplified through gene amplification reactions.

The primers useful in the present invention are hybridized or annealed in a portion of a template to a form double stranded structure. To form the double stranded structure, the suitable conditions of nucleic acid hybridization are disclosed in several previous arts described above.

The term "hybridizing" used herein refers to the formation of a duplex structure from a complementary base pairing between two single stranded nucleic acids. The hybridization may occur between single stranded nucleic acid strands perfectly matched or substantially matched with some mismatches. The complementarity for hybridization may depend on hybridization conditions, particularly temperature. There is no intended distinction between the terms "annealing" and "hybridizing", and these terms will be used interchangeably.

A variety of DNA polymerases can be used in the amplification of the present method, which includes "Klenow" fragment of *E. coli* DNA polymerase I, a thermostable DNA polymerase, and bacteriophage T7 DNA polymerase. Practically, the polymerase is a thermostable DNA polymerase which may be obtained from a variety of bacterial species, including *Thermus aquaticus*(Taq), *Thermus thermophilus* (Tth), *Thermus filiformis*, *Thermis flavus*, *Thermococcus literalis*, *Pyrococcus furiosus*(Pfu), *Thermus antranikianii*, *Thermus caldophilus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana* and *Thermosipho africanus*, but is not limited to.

When a polymerization reaction is being conducted, it is preferable to provide the components required for such reaction in excess in the reaction vessel. Excess in reference to components of the extension reaction refers to an amount of each component such that the ability to achieve the desired extension is not substantially limited by the concentration of that component. It is desirable to provide to the reaction mixture amount of required cofactors such as $Mg^{2+}$, dATP, dCTP, dGTP, and dTTP in sufficient quantity to support the degree of the extension desired. All of the enzymes used in the amplification reaction may be active under the same reaction conditions. Indeed, buffers exist in which all enzymes are near their optimal reaction conditions. Therefore, the amplification processes of the present invention can be done in a single reaction volume without any change of conditions such as addition of reactants.

The annealing in the present method is performed under stringent conditions that allow for specific binding between a target nucleotide sequence and primers. Such stringent conditions for annealing will be sequence-dependent and varied depending on environmental parameters.

Gel electrophoresis of the amplified reaction products is run and the resulting bands are observed and analyzed, thereby enabling to confirm the expression or presence of a target gene (for example, oncogenic genes).

Effects of this Invention

The features and advantages of this invention are summarized as follows:
(a) The present invention relates to a method for treating cancer by using siRNA nanocomplex containing a pharmaceutical composition, a drug delivery system.

(b) The present nanocomplex consists of a nucleic acid molecule, a monocationic drug and a biocompatible polymer surfactant, and not only has a hydrodynamic size of 10 nm or less, but uniformly distributes as a colloidal form in an aqueous environment.

(c) In addition, the nanoscale colloidal formulation of the present invention could protect the nucleic acid molecule from a nuclease (for example, serum nucleases) rich in a physiological environment through the formulation of a stable monocomplex, and provide improvement of cell penetration and in vivo delivery via a micellar structure as well as further protection of the nucleic acid molecule by a micellar passivation.

(d) Therefore, the present nanocomplex and a composition and system using the same can deliver an active ingredient (for example, a nucleic acid molecule and monocationic drug) into a cell/tissue of interest in a stable manner, and may be effectively applied for treating or detecting diverse disorders (practically, cancers).

BRIEF DESCRIPTION OF THE DRAWINGS

FIGS. 1a, 1b, 1c and 1d are schematic illustrations of ternary HMplexation (1a) and colloidal characteristics of the resulting ternary HMplexes (1b-1d): (1b) TEM image; (1c) Hydrodynamic size (open circle) and zeta potential (solid square) measured by DLS; and (1d) Agarose gel electrophoresis of HMplexes prepared at various charge ratios indicated (N/P=BZT ammonium/siRNA phosphate) in PBS (pH 7.4).

FIG. 2 represents hydrodynamic sizes of siRNA/BZT binary complexes (without F-68) at charge ratios of 1, 2 and 5 (N/P=BZT ammonium/siRNA phosphate), measured by DLS.

FIG. 3a shows an agarose gel electrophoresis of free siRNA and ternary HMplexes, both of which were incubated in 50% of serum at 37° C. for the indicated times. After 24 h serum incubation, HMplexes were decomplexed with 200 μg heparin sodium. The rightmost panel shows the released intact siRNA that was protected by ternary HMplexation against nucleases in serum. FIG. 3b is a heparin polyanion competition assay for siRNA/BZT nanocomplexes with and without micellar encapsulation by F-68. Samples were treated with various amounts of heparin sodium for 30 min at room temperature. Control (C) is free siRNA. FIG. 3c is fluorescence spectra of ternary HMplexes prepared with Cy5.5-labeled siRNA ($\lambda_{ex}$=670 nm), with and without heparin treatment for 30 min.

FIG. 4 is optical and NIRF images of MDA-MB-231 cells treated with ternary HMplexes prepared with Cy5.5-labeled siRNA (left column) or Cy5.5-labeled F-68 (right column) for 1 h and 4 h at 37° C.

FIG. 5 shows fluorescence microscopic images of MDA-MB-231 cells treated for 4 h with ternary HMplexes composed of TAMRA-labeled siRNA, BZT and Cy5.5-labeled F-68.

FIG. 6a represents a down-regulation of Bcl-2 gene expression in MDA-MB-231 cells analyzed by semi-quantitive RT-PCR. The Bcl-2 mRNA level was plotted after normalizing with the gene expression intensity of 1-actin. FIG. 6b is a flow cytometric analysis on apoptosis induced in MDA-MB-231 cells treated with ternary HMplexes of siRNA or scRNA. Apoptotic cells were stained with FITC-labeled annexin V. FIG. 6c is a cytotoxicity of ternary HMplexes (siRNA) against normal cells (NIH-3T3 and MRC-5) and cancer cells (MDA-MB-231), evaluated by the colorimetric MTT assay.

FIG. 7a is in vivo NIRF images showing tumor accumulation of ternary HMplexes prepared with Cy5.5-labeled siRNA that were injected peritumorally to MDA-MB-231 xenograft mice ($\lambda_{ex}$=675 nm, $\lambda_{em}$=720 nm). FIG. 7b shows low (×200) and high (×1000) magnification histological micrographs of tumor sections resected at 4 d after peritumoral injection of free Cy5.5-labeled siRNA or HMplexes made of Cy5.5-siRNA. The fluorescence signals of Cy5.5-siRNA and DAPI-stained nuclei are presented in red and blue, respectively.

FIG. 8 is in vivo NIRF images showing tumor accumulation of free Cy5.5-labeled siRNA that was injected peritumorally to MDA-MB-231 xenograft mice ($\lambda_{ex}$=675 nm, $\lambda_{em}$=720 nm).

FIGS. 9a and 9b are results representing tumor growth suppression (9a) and body weight changes (9b) for 30 d in MDA-MB-231 xenografts mice peritumorally injected with Bcl-2 targeting or nontargeting HMplexes (HMplex/siRNA or HMplex/scRNA) or untreated (control).

DETAILED DESCRIPTION OF THIS INVENTION

The present invention will now be described in further detail by examples. It would be obvious to those skilled in the art that these examples are intended to be more concretely illustrative and the scope of the present invention as set forth in the appended claims is not limited to or by the examples.

Examples Experimental Materials and Methods Experimental Materials

All chemicals were purchased from Sigma-Aldrich (St. Louis, Mo., USA), and used without further purification. Lipofectamine 2000 and SYBR® Gold were purchased from Invitrogen (Carlsbad, Calif., USA) and used according to the manufacturer's instructions. Custom Bcl-2 siRNA (sense 5'-GUACAUCCAUUAUAAGCUG (SEQ ID NO: 1)-dTdT; antisense CAGCUUAUAAUGGAUGUAC (SEQ ID NO: 2)-dTdT), scrambled siRNA (scRNA, AccuTarget™ Negative Control siRNA), Cy5.5- or TAMRA-labeled siRNA end PCR premix (AccuPower® PCR PreMix) were available from Bioneer (Daejeon, Korea). For near-infrared fluorescence (NIRF) labeling of F-68, vinylsulfone-functionalized Cy5.5 (Cy5.5-VS, BioActs Co. Ltd., Korea) was conjugated to the hydroxyl group of F-68 by mixing F-68 (100 mg) and Cy5.5-VS (0.5 mg) in PBS (pH 8.0) for 2 h at room temperature. The Cy5.5-labeled F-68 was dialyzed against Milli-Q water in a cellulose ester membrane (Spectra/Por Membrane®, MWCO: 3.5 kDa) for 1 d and then lyophilized.

Preparation and Characterization of HMplex

HMplexes were prepared by mixing 9.3 μg of siRNA (or scRNA) and varying amounts of BZT (23.8-476.8 μg) in the presence or absence of Pluronic F-68 (2.5 mg) in 500 μL PBS (pH 7.4) for 3 h at room temperature, which resulted in various charge ratios (N/P=BZT ammonium/siRNA phosphate=1-20). For fluorescence labelling of the HMplexes, Cy5.5-labeled F-68 or Cy5.5-labeled siRNA was used for complexation. Transmission electron microscopic (TEM) images were recorded with a CM30 electron microscope (FEI/Philips) operated at 200 kV. For the TEM sample preparation, a drop of sample dispersion was dried on a 200 mesh copper grid coated with carbon and negatively stained with a 2 wt % uranyl acetate solution. The hydrodynamic size and zeta potential of HMplexes were determined using a zeta-sizer (Nano-ZS, Malvern, UK). For gel retardation assay, HMplexes were loaded onto 2% agarose gel and electrophoresis was performed in TBE buffer solution at 100 V. After electrophoresis, the SYBR Gold-stained siRNA bands were visualized using a gel documentation system (MiniBis Pro, DNR Bio-Imaging Systems, Israel). All the in vitro and in vivo experiments were performed with HMplexes at a fixed charge ratio (N/P=4).

Cell Culture

Cell culture media, antibiotics, fetal bovine serum (FBS) and bovine calf serum (BCS) were purchased from Welgene Inc. (Korea). NIH3T3 (a mouse embryonic fibroblast cell line), MRC-5 (a human fetal lung fibroblast cells) and human TNBC cells (MDA-MB-231) were cultured according to the manufacturer's specifications. MRC-5 was maintained in DMEM (Dulbecco's modified eagle medium) with 10% FBS, L-glutamine ($5 \times 10^{-3}$ M) and gentamicin (5 µg/mL), in a humidified 5% $CO_2$ incubator at 37° C. MDA-MB-231 and NIH-3T3 were maintained in RPMI 1640 medium supplemented with 10% serum (FBS for MDA-MB-231 or BCS for NIH-3T3), L-glutamine ($5 \times 10^{-3}$ M) and gentamicin (5 µg/mL) in a humidified 5% $CO_2$ incubator at 37° C.

Evaluation of In Vitro Cytotoxicity and Stability

In vitro cytotoxicity studies of HMplexes were performed against normal cells (MRC-5 and NIH-3T3) and cancer cells (MDA-MB-231) using the colorimetric MTT assay. Cells were treated with HMplexes at various concentrations for 4 h and then incubated in a serum-free medium for another 44 h after washing twice with cold PBS (pH 7.4). After washing with PBS, the cells were treated with MTT reagents and the absorbance at 540 nm was measured with a microplate reader (Spectra Max 340, Molecular Devices, Sunnyvale, Calif., USA). The complex stability of HMplexes was evaluated by a heparin polyanion competition assay and a serum stability assay. For the heparin polyanion competition assay, HMplexes containing 1 µg siRNA were incubated with varying amounts of heparin (0-200 µg) for 30 min at room temperature and then subjected to 2% agarose gel electrophoresis. The decomplexed siRNA was detected with SYBR Gold staining. For serum stability studies, HMplexes or naked siRNA were incubated in 50% FBS/PBS (pH 7.4) at 37° C. for predetermined time periods (0-24 h). Aliquots from each sample were analyzed by 2% agarose gel electrophoresis and visualized with SYBR Gold.

In Vitro Cellular Uptake and Evaluation of Apoptosis

MDA-MB-231 cells were seeded onto 35 mm coverglass bottom dishes ($2 \times 10^5$ cells). At a confluence of 70-80%, cells were treated with free Cy5.5-siRNA or HMplexes of Cy5.5-siRNA for 1 h or 4 h in a serum-free medium. Afterward, cells were washed twice with cold PBS (pH 7.4) and fixed with 4% (v/v) paraformaldehyde. Fluorescence images were taken using a LEICA DMI3000B equipped with a Nuance FX multispectral imaging system (CRI, USA). For determination of apoptosis, MDA-MB-231 cells were seeded on 6-well culture plates ($2 \times 10^5$ cells) and incubated for 12 h. After treatment with HMplexes of siRNA or scRNA for 2 h in a serum-free medium, the cells were washed twice with cold PBS (pH 7.4) and incubated for another 44 h. Then the cells were washed twice with cold PBS (pH 7.4) and collected by centrifugation. Annexin V-FITC (BioVision, Inc., USA) was added into the cells for selectively staining apoptotic cells following a literature procedure [8]. Green fluorescence intensity of the stained apoptotic cells was analyzed on flow cytometry (Guava easyCyte™ Flow Cytometers, EMD Millipore, USA).

Evaluation of Bcl-2 Down-Regulation

The in vitro gene silencing by HMplexes was assessed using semi-quantitative reverse transcription-PCR (RT-PCR). MDA-MB-231 cells were seeded on 6-well culture plates ($2 \times 10^5$ cells) and incubated for 12 h. At a confluence of 70-80%, HMplexes of siRNA or scRNA were added into the cells at a final RNA concentration of 140 nM. After incubation of 2 h in a serum-free medium, the cells were washed twice with cold PBS (pH 7.4) and incubated for another 44 h. Then the cells were collected by centrifugation and total RNA was isolated using RNeasy Mini Kit (Qiagen, Hilden, Germany) following the manufacturer's instructions. Down-regulation of Bcl-2 mRNA was determined by normalizing Bcl-2 expression levels to the endogenous actin levels under the following conditions of semi-quantitative RT-PCR in PCR premix by using Veriti® 96-Well Thermal Cycler (Applied Biosystems, Foster City, Calif.): a total of 25 cycles consisting of 94° C. for 60 s, 50° C. for 60 s, and 72° C. for 60 s, with a final extension step for 10 min at 72° C. Results were presented as average of at least 3 independent experiments. Custom primers for Bcl-2 and β-actin were as follows.

```
1) Bcl-2,
sense
5'-CGACGACTTCTCCCGCCGCTACCGC-3',
and antisense
5'-CCGCATGCTGGGGCCGTACAGTTCC-3';
and 2) β-actin,
sense
5'-GCTCGTCGTCGACAACGGCTC-3',
and antisense
5'-CAAACATGATCTGGGTCATCTTCTC-3'.
```

In Vivo Studies on Stability, Peritumoral Delivery and Tumor Growth Inhibition

Animal experiments were performed according to the guidelines established by Korea Institute of Science and Technology (KIST). For animal experiments, Crlj nude mice (5-week-old female; Orient Bio Inc., Korea) were anaesthetized with intraperitoneal injection of 0.5% pentobarbital sodium (0.010 mug). For tumor xenograft model, MDA-MB-231 cells ($1.0 \times 10^7$ cells) were inoculated into the flank of mice by subcutaneous injection. For in vivo stability test, HMplexes (60 µL, 140 nM siRNA) were injected into a tumor xenograft mouse model by peritumoral route (n=3/group). In vivo fluorescence images were taken at predetermined time points by an IVIS Spectrum imaging system (Caliper, USA). To examine the intratumoral distribution of the peritumorally applied HMplexes, tumors were excised from the mice, fixed in neutral buffered formalin and embedded in paraffin. The tissue blocks were cut into 5 µm sections and fluorescence images were taken by a LEICA DMI3000B equipped with a Nuance FX multispectral imaging system (CRI, USA). Tumor growth inhibition was observed by measuring the tumor volume. When the tumor volume reached approximately 50 $mm^3$, HMplexes (6 mg/kg body-weight) were administered locally by peritumoral route (day 1) and the local administration was repeated on day 4 and 6. Tumor volume and weight were recorded over a period of 4 weeks (n=3/group).

Results

Design of siRNA/Drug HMplex Formulation

The HMplex-based siRNA/drug co-delivery formulation has been designed as a self-assembled ternary complex composed of three active components (FIG. 1a). As a monocationic surfactant, we selected benzethonium chloride (BZT) that has been reported to induce cancer-specific apoptosis by activating caspase-2, caspase-8, caspase-9 and caspase-3. Herein, BZT plays dual functions, i.e., acts not only as a surfactant for the HMplex formation but also as an anticancer agent by itself. Hence, it can get rid of the necessity of using separate anticancer agents and cytotoxic monocationic surfactants, which simplifies the co-delivery constitution as well as minimizes its nonspecific cytotoxicity. For genetic chemosensitization, BZT was complexed with Bcl-2 targeting siRNA. Silencing the Bcl-2 gene has been recognized as a promising target for chemosensitization because the anti-apoptotic Bcl-2 protein is overexpressed in 50-70% of all human cancers and makes them resistant to the treatment by chemodrugs and radiation [9]. Therefore, the combination of BZT with Bcl-2 siRNA would present a synergistic effect of treatment by sensitizing resistant cancer cells to the anticancer action of BZT. Finally, the organic-soluble binary HMplex formed between Bcl-2 siRNA and BZT was further formulated into the ternary HMplex by encapsulating with micelles of a biocompatible polymeric surfactant, Pluronic F-68 (U.S. FDA approved as a local/i.v. injectable pharmaceutical ingredient), which would improve the complex stability as well as the efficiencies of cell penetration and in vivo delivery.

The colloidal size is an important parameter that governs the tumor-targeting efficiency of nanotherapeutics. Tumor tissues have a special microenvironment composed of dense interstitial matrix where interstitial hypertension hinders passive diffusion of nanoparticles, restricting deep penetration into the tumor. Recent studies revealed that smaller nanoparticles show higher rates of tumor permeation. In this regard, further micellar formulation of the HMplex with F-68 allows us to miniaturize the ternary complex to increase the intratumoral diffusion and penetration efficiency.

Formation and Characteristics of Ternary HMplexes

When water-soluble siRNA and BZT were mixed in water, water-insoluble binary complexes formed spontaneously in a form of big nanoaggregates with a hydrodynamic size of 200-500 nm (FIG. 2). In the presence of pre-dissolved Pluronic F-68, however, the mixing of siRNA and BZT produced much smaller colloids with no big aggregates, as designed for the colloidal size minimization. As sketched in FIG. 1a, the HMplexation is composed of two sequential processes: 1) multiple monocomplexation-induced hydrophobic association between the oppositely charged counterparts into big nanoaggregates (binary complexation); and 2) micellar dissolution and encapsulation of the binary complexes into the surfactant-passivated tiny nanoparticles (ternary complexation). Transmission electron microscopy (TEM) and dynamic light scattering (DLS) studies manifested that the resulting ternary HMplex was indeed greatly miniaturized by micellar encapsulation (smaller than 10 nm; FIGS. 1b and 1c), being suitable for facile penetration into the dense tumor tissue.

With increasing charge ratio (N/P=BZT ammonium/siRNA phosphate; increasing BZT while keeping the siRNA amount constant) in the presence of F-68, the zeta potential of the ternary HMplex was gradually inverted from negative to positive values with a slight increase in the hydrodynamic size (FIG. 1c). The gradual changes in both the surface charge and size reached saturation at above a charge ratio of 5 or more, suggesting that the ternary HMplexation is efficient and can be completed at a fairly low N/P ratio. The efficient HMplex formation was confirmed by the gel retardation assay with varying charge ratio (FIG. 1d). At charge ratios of 2 or higher, uncomplexed free siRNA was completely absent, demonstrating that all the siRNA chains were HMplexed by excess BZT. Owing to the charge reversal and size increase by HMplexation, the migration of siRNA through the gel was greatly retarded under the applied electric field, with the HMplex bands remaining at the loading slots. Importantly, the retarded HMplex bands showed no staining with an intercalating dye (SYBR® Gold), as generally observed in strongly interacting DNA/surfactant complexes. This suggests that the cationic intercalating dye is not accessible to the HMplexed siRNA because siRNA chains are tightly packed and passivated within the HMplex structure through the strong collective interactions with BZT and F-68.

Protection of siRNA by Ternary HMplexation

The susceptibility of siRNA toward degradation in nuclease-rich serum was compared between the ternary HMplex (N/P=4) and free siRNA by incubating them in 50% serum media at 37° C. At each predetermined time point, an aliquot was sampled and analyzed by gel electrophoresis. As shown in FIG. 3a, free siRNA was gradually degraded with time in serum and completely disappeared at 24 h. In contrast, the HMplexed siRNA presented improved stability with no notable sign of degradation or decomplexation into free siRNA during serum incubation. Upon induced decomplexation by heparin treatment, intact free siRNA was released from the serum-treated HMplexes even after 24 h treatment, confirming the effective protection of siRNA by HMplexation.

To evaluate the micellar shielding effect on the complex stability, HMplexes (NIP=4) with and without F-68 encapsulation were treated with varying concentrations of heparin sodium and the induced decomplexation by competition between siRNA and heparin was monitored by gel electrophoresis (FIG. 3b). It was shown that the binary siRNA/BZT HMplex without F-68 began to release decomplexed siRNA even at a low concentration of heparin (10 μg). In sharp contrast, the ternary HMplex with F-68 passivation disassembled only at much higher heparin concentrations, unambiguously attributed to the micellar shielding effect which blocks the competition between the complexed siRNA and external polyanions.

The decomplexation feature was further examined by using Cy5.5-labeled siRNA in HMplexation. As shown in FIG. 3c, the intense near-infrared fluorescence (NIRF) of free Cy5.5-siRNA was totally quenched by ternary HMplexation. When heparin was added to the nonfluorescent HMplex, the original fluorescence signal of Cy5.5-siRNA (an indicative factor of siRNA release depending on the formation of HMplexation) was recovered depending on the heparin amount, indicative of the siRNA release by decomplexation of HMplexes. The initial formation of nonfluorescent HMplex is attributed to the self-quenching of fluorescence typical of common organic dyes in the aggregated state, clearly evidencing that the multiple monocomplexed Cy5.5-siRNA/BZT chains were closely aggregated by strong hydrophobic association with each other to construct the compact and stable HMplex nanostructure.

Intracellular Uptake of HMplexes

Cell internalization of HMplexes was examined with TNBC cells (MDA-MB-231) by using Cy5.5-labeled ternary complexes (N/P=4). Cy5.5 was labeled to either siRNA or F-68 to prepare Cy5.5-siRNA/BZT/F-68 or siRNA/BZT/Cy5.5-F-68 for NIRF tracking of siRNA or F-68, respectively (FIG. 4). At an early stage of cell treatment (1 h), the F-68 signals were mostly localized near the cell membrane whereas the siRNA fluorescence was not dearly observed due to the low intensity. As discussed in FIG. 3c, the quenched fluorescence of siRNA suggests that the densely complexed HMplex preserved its structural integrity at an early stage of cell internalization. After 4 h treatment, however, the siRNA fluorescence was recovered and diffusely seen in the cytoplasm. The distribution of F-68 signals was also shifted to the similar cytoplasmic region, being seemingly colocalized with siRNA (FIG. 5). It is highly probable that the transfected HMplex was decomplexed in the cytoplasmic environment and thereby free siRNA and BZT were released from the dense complex to regain the fluorescence intensity of free Cy5.5-siRNA.

Bcl-2 Gene Silencing and Sensitization to Apoptosis

Human TNBC cells (MDA-MB-231) are known to overexpress Bcl-2 proteins which inhibit the apoptosis pathway and develop resistance to treatment. As demonstrated in FIG. 4, ternary HMplexes are capable of transfection and release of Bcl-2 targeting siRNA into the cytoplasmic area of TNBC cells, which are key requirements for the successful RNA interference by siRNA delivery [1-4]. Moreover, it is reasonably speculated that the co-complexed BZT is concomitantly released intracellularly to trigger apoptosis. Hence, we explored potential of the ternary HMplex (N/P=4) for siRNA-mediated Bcl-2 gene silencing and thereby chemosensitization of TNBC cells to apoptosis induction by the co-delivered BZT. For this, TNBC cells were treated with siRNA complexes for 2 h and incubated for another 44 h after washing the samples. FIG. 6a displays the result of Bcl-2 down-regulation in TNBC cells depending on the siRNA formulation. HMplexes of non-targeting scrambled siRNA (scRNA) showed a minute silencing effect on Bcl-2 expression (about 80% with respect to the untreated control level), which is possibly due to the cytotoxicity of the co-delivered BZT against TNBC cells. With genetic targeting by HMplexes of Bcl-2 siRNA, TNBC cells showed a remarkably reduced level of Bcl-2 expression down to about 20%, which is even more efficient than a standard siRNA delivery system (Lipofectamine).

The sensitized induction of apoptosis by siRNA/BZT co-delivery was evaluated with MDA-MB 231 cells by flow cytometry (FIG. 6b). HMplexes of non-targeting scRNA (HMplex/scRNA) presented a minute increase in the population of apoptotic cells, again reflecting the cancer-specific toxicity of BZT. Importantly, the level of apoptosis was greatly increased by treatment with HMplexes of Bcl-2 targeting siRNA. This result confirms that Bcl-2 gene targeting by the delivered siRNA remarkably sensitized the resistant cancer cells to anticancer effect of the co-delivered BZT, validating our HMplex-based design strategy for the synergistically enhanced combination therapy. It is noteworthy that the HMplex between Bcl-2 siRNA and BZT manifested a significant anticancer effect on TNBC cells (MDA-MB-231) with no notable nonspecific toxicity against normal cells (NIH-3T3 and MRC-5), which makes it a potential therapeutic formulation candidate with clinical utility (FIG. 6c).

In Vivo Tumor Delivery by Peritumoral Injection

In vivo therapeutic utility of the co-delivering HMplex was explored with human triple-negative breast tumor (MDA-MB-231) xenografts in mice. HMplexes were administered by peritumoral route to examine their intratumoral penetration and accumulation. Peritumoral administration route was chosen because it offers benefits for treating localized tumors by adjuvant chemotherapy prior to or after a local treatment such as surgery. In general, systemic administration of therapeutic nanoparticles often causes side effects and requires high dosage due to a variety of reasons such as filtration loss by the reticuloendothelial system (RES) or limited systemic blood flow directed to the tumor. Direct intratumoral injection is the most common route for local delivery of chemodrugs but has limitation such as drug effusion from the injection area of tumor. Peritumoral injection sometimes showed better anticancer effects than intratumoral route, and can offer an opportunity to treat undetected cancer cells hidden in the surgical margin. However, peritumoral application still demands better nanoparticles with higher tumor penetration that can overcome physical barriers at the periphery of solid tumors. In this respect, we applied our HMplex to peritumoral administration for locoregional chemotherapy because its small colloidal size and Pluronic-coated surface would facilitate deep penetration into the tumor by helping to cross the peripheral barriers.

FIG. 7a shows the tumor accumulation behavior of the peritumorally injected HMplex. For comparison, free Cy5.5-siRNA and HMplexes of Cy5.5-siRNA (N/P=4) were administered to MDA-MB-231 xenograft mice by peritumoral injection and the NIRF signals were monitored by an IVIS imaging system. Free Cy5.5-siRNA without HMplexation displayed weak fluorescence from the tumor at 1.5 h post-injection, which was further reduced with time (FIG. 8). This implies low in vivo stability of naked siRNA or its clearance due to low tumor accumulation. In sharp contrast, HMplexes containing the same amount of Bcl-2 siRNA exhibited recovery of the initially self-quenched Cy5.5-siRNA fluorescence from the tumor after peritumoral injection, elucidating that HMplexes were internalized into the tumor and decomplexed to release fluorescent siRNA chains as discussed in FIG. 2c. The recovered tumor signal reached a maximum intensity at 1-3 h after injection and then gradually decreased. Nonetheless, a notable signal was detected from the tumor even at 6 d post-injection, indicative of successful in vivo stabilization and peritumoral delivery of siRNA by ternary HMplexation. To confirm this argument, histological examination was done with tumor sections excised at 4 d after peritumoral injection of free Cy5.5-siRNA or HMplexes containing the same amount of Cy5.5-siRNA (FIG. 7b). In the case of HMplexes, clear Cy5.5-siRNA signals were observed in the cytoplasm of cancer cells (distinct from the DAPI-stained nuclear areas), strongly supporting that the decomplexation between siRNA and BZT occurred after cell internalization. This contrasts strikingly to the negligible cytoplasmic signal of the tumor sections from mice treated with naked Cy5.5-siRNA. From all these results, it is concluded that ternary HMplexes indeed co-deliver siRNA and BZT from the peritumoral exterior into the tumor tissue and further to the cytoplasm of cancer cells in vivo.

Tumor Suppression by HMplexes in MDA-MB-231 Xenografts

Finally, the in vivo tumor suppression effect was comparatively assessed with HMplexes (N/P=4) of Bcl-2 siRNA or scRNA. The HMplex samples were administered to MDA-MB-231 xenograft mice in triple doses by peritumoral injection on day 1, 4 and 6, and the tumor growth and body weights were monitored for 30 d (FIG. 9). As shown in FIG. 6a, the experimental group treated with HMplexes of Bcl-2 targeting siRNA (HMplex/siRNA) exhibited a significant tumor suppression effect which was sustained throughout the experimental period. It is noted that HMplexes of nontargeting scRNA (HMplex/scRNA) also presented tumor suppression to some extent, most probably due to the anticancer effect of the co-complexed BZT as found in vitro (FIG. 6). In spite of the apoptosis-inducing BZT effect, both HMplexes showed no toxic impact on the animal viability, as monitored with the minimal body weight changes during the experiment (FIG. 9b). Importantly, the suppressed tumor volume by HMplex/siRNA at the end of treatment (205 mm$^3$) is less than half of the value reached by HMplex/scRNA (440 mm$^3$), clearly evidencing that combining gene-targeting RNAi and chemotherapy by the co-delivering HMplex is indeed operative in vivo to synergistically enhance the treatment efficacy for locoregional chemotherapy of resistant TNBC.

Advantages and Benefits of the Present Invention

We have developed a simple and biocompatible formulation for the siRNA/drug co-delivery, based on multiple monocomplexation-induced hydrophobic associations between Bcl-2 targeting siRNA and a monocationic anticancer agent (BZT). It was found that the physical mixing of siRNA, BZT and Pluronic F-68 causes spontaneous formation of a tightly complexed nanostructure owing to the strong cooperative electrostatic/hydrophobic interactions between the ingredients. By virtue of the resulting compact complexation with micellar passivation as well as small colloidal size less than nm, the ternary HMplex was capable of suitable protection of siRNA and successful in vivo co-delivery of siRNA and BZT into the cytoplasm of cancer cells by peritumoral administration. It was shown in vitro and in vivo that cell-internalized HMplexes are decomplexed and release payloads in the cytoplasm to trigger a cooperative action, i.e., silencing anti-apoptotic Bcl-2 by siRNA and thereby sensitized induction of apoptosis by BZT. Thanks to this gene-targeted chemosensitization and cancer-specific toxicity of BZT, the co-delivering HMplex presented a synergistically enhanced therapeutic effect on the aggressive and resistant TNBC model in mice, demonstrating potential for locoregional cancer treatment by targeted combination therapy.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating cancer comprising the steps of:
administrating to a subject in need thereof a nanocomplex comprising
   (i) a hydrophobically associated multiple monocomplex (HMplex) formed through self-assembly of a nucleic acid molecule selected from siRNAs with 19 to 100 nucleotides and benzethonium chloride (BZT) which is a monocationic drug and
   (ii) polyoxyethylene-polyoxypropylene-polyoxyethylene block copolymer which encapsulates the HMplex,
   wherein the siRNAs inhibit the expression of a gene selected from the group consisting of Bcl-2, Bcl-3, Bcl-4, Bcl-5, Bcl-6, HER2/Neu, HER3, HER4, raf, c-fos, c-jun, c-kit, c-met, c-ret, hTERT, and erbB,
   wherein the nanocomplex has a hydrodynamic size of 5 nm or more and 10 nm or less.

2. The method of claim 1, wherein the HMplex, the self-assembly of the nucleic acid molecule and the BZT, is formed through electrostatic interaction.

3. The method of claim 2, wherein a charge ratio of the BZT to the nucleic acid molecule is 2 or more.

4. The method of claim 1, wherein the polyoxyethylene-polyoxypropylene-polyoxyethylene block copolymer is a pluronic poloxamer selected from the group of pluronic F-68, F-38, F-77, F-98, F108 and F-127.

5. The method of claim 1, wherein the cancer is any one cancer selected from the group consisting of brain cancer, neuroendocrine cancer, stomach cancer, lung cancer, breast cancer, ovarian cancer, liver cancer, Laryngeal cancer, pancreatic cancer, bladder cancer, adrenal cancer, colon cancer, colon cancer, cervical cancer, prostate cancer, bone cancer, skin cancer, thyroid cancer, parathyroid cancer or ureteral cancer.

6. The method of claim 1, wherein the administration is parenteral administration.

7. The method of claim 6, wherein the parenteral administration is any one selected from peritumoral administration, intravenous administration and intraperitoneal administration.

8. The method of claim 7, wherein the subject is a mammal.

9. A method for delivering benzethonium chloride (BZT) comprising the steps of:
administrating to a subject in need thereof a nanocomplex comprising
   (i) a hydrophobically associated multiple monocomplex (HMplex) formed through self-assembly of a nucleic acid molecule selected from siRNAs with 19 to 100 nucleotides and benzethonium chloride (BZT) which is a monocationic drug and
   (ii) polyoxyethylene-polyoxypropylene-polyoxyethylene block copolymer which encapsulates the HMplex,
   wherein the siRNAs inhibit the expression of a gene selected from the group consisting of Bcl-2, Bcl-3, Bcl-4, Bcl-5, Bcl-6, HER2/Neu, HER3, HER4, raf, c-fos, c-jun, c-kit, c-met, c-ret, hTERT, and erbB,
   wherein the nanocomplex has a hydrodynamic size of 5 nm or more and 10 nm or less.

10. The method of claim 9, wherein the administration is parenteral administration.

11. The method of claim 10, wherein the parenteral administration is peritumoral administration, intravenous administration, or intraperitoneal administration.

* * * * *

SEQUENCE LISTING

<160> NUMBER OF SEQ ID NOS: 6

<210> SEQ ID NO 1
<211> LENGTH: 19
<212> TYPE: RNA
<213> ORGANISM: Artificial Sequence
<220> FEATURE:
<223> OTHER INFORMATION: Synthesized

<400> SEQUENCE: 1
guacauccau uauaagcug                                                19

<210> SEQ ID NO 2
<211> LENGTH: 19
<212> TYPE: RNA
<213> ORGANISM: Artificial Sequence
<220> FEATURE:
<223> OTHER INFORMATION: Synthesized

<400> SEQUENCE: 2
cagcuuauaa uggauguac                                                19

<210> SEQ ID NO 3
<211> LENGTH: 25
<212> TYPE: DNA
<213> ORGANISM: Artificial Sequence
<220> FEATURE:
<223> OTHER INFORMATION: Synthesized

<400> SEQUENCE: 3
cgacgacttc tcccgccgct accgc                                         25

<210> SEQ ID NO 4
<211> LENGTH: 25
<212> TYPE: DNA
<213> ORGANISM: Artificial Sequence
<220> FEATURE:
<223> OTHER INFORMATION: Synthesized

<400> SEQUENCE: 4
ccgcatgctg gggccgtaca gttcc                                         25

```
<210> SEQ ID NO 5
<211> LENGTH: 21
<212> TYPE: DNA
<213> ORGANISM: Artificial Sequence
<220> FEATURE:
<223> OTHER INFORMATION: Synthesized

<400> SEQUENCE: 5
gctcgtcgtc gacaacggct c                                           21

<210> SEQ ID NO 6
<211> LENGTH: 25
<212> TYPE: DNA
<213> ORGANISM: Artificial Sequence
<220> FEATURE:
<223> OTHER INFORMATION: Synthesized

<400> SEQUENCE: 6
caaacatgat ctgggtcatc ttctc                                       25
```